(12) United States Patent
Bauchet et al.

(10) Patent No.: US 8,459,118 B2
(45) Date of Patent: Jun. 11, 2013

(54) PROCESS TO MONITOR UNWANTED FORMATION OF A POLYMER HAVING INTERNAL STRAIN BY ACOUSTIC EMISSION ANALYSIS

(75) Inventors: Jean-Pierre Thoret Bauchet, Brussels (BE); Gustav Alcuri, Dame Marie (FR)

(73) Assignee: Total Petrochemicals Research Feluy, Seneffe (Feluy) (BE)

( * ) Notice: Subject to any disclaimer, the term of this patent is extended or adjusted under 35 U.S.C. 154(b) by 363 days.

(21) Appl. No.: 12/522,052

(22) PCT Filed: Jan. 8, 2008

(86) PCT No.: PCT/EP2008/050141
§ 371 (c)(1), (2), (4) Date: Feb. 5, 2010

(87) PCT Pub. No.: WO2008/084045
PCT Pub. Date: Jul. 17, 2008

(65) Prior Publication Data
US 2010/0162816 A1   Jul. 1, 2010

(30) Foreign Application Priority Data
Jan. 9, 2007  (EP) .................................... 07100265

(51) Int. Cl.
*G01N 29/14* (2006.01)
(52) U.S. Cl.
USPC .......................................................... 73/587
(58) Field of Classification Search
USPC .......................................................... 73/587
See application file for complete search history.

(56) References Cited

U.S. PATENT DOCUMENTS 5,945,032 A * 8/1999 Breitenbach et al. .... 252/186.29
6,770,222 B1   8/2004 Ukita et al.
2002/0067840 A1 * 6/2002 Kobayashi .................... 381/111
2003/0121330 A1 * 7/2003 Muhle et al. .................... 73/600
2007/0060721 A1   3/2007 Muhle et al.

FOREIGN PATENT DOCUMENTS

| DE | 241480 | 12/1986 |
|---|---|---|
| DE | 241480 A1 | 12/1986 |
| EP | 0 297 729 A2 | 1/1989 |
| GB | 2038851 | 7/1980 |
| WO | 03/051929 A1 | 6/2003 |
| WO | WO 03/051929 | 6/2003 |
| WO | 2007/037815 A1 | 4/2007 |

OTHER PUBLICATIONS

Relating Acoustic Emission Signal Parameters to the Strength of Fibres used in the Manufacture of Polymeric Composites; E.U. Okaraafar and R. Hill; Sep. 1994; Elsevier Sdcnce B.Y; p. 123-131.*
Okoroafor E U et al: "Relating Acoustic Emission Signal Parameters to the Strength of Fibres used in the Manufacture of Polymeric Composites" Ultrasonics, IPC Science and Tech.
International Search Report for International Application No. PCT/EP2008/050141, mailed on Apr. 25, 2008 (2 pages).
Okoroafor, et al., "Relating acoustic emission signal parameters to the strength of fibres used in the manufacture of polymeric composites", Ultrasonics, IPC Science and Technology Press Ltd. Guildford, GB, vol. 33, No. 2, 1995, pp. 123-131, XP004035590 (9 pages).
Office Action issued in Japanese Application No. 2009-544420 mailed on Sep. 13, 2011, and English translation thereof (6 pages).
Office Action issued in Japanese Application No. 2009-544420 mailed on Jan. 24, 2012, and English translation thereof (9 pages).
Patent Abstracts of Japan, Publication No. 03-269221, Publication Date: Nov. 29, 1991, 1 page.
Patent Abstracts of Japan, Publication No. 02-242149, Publication Date: Sep. 26, 1990, 1 page.

* cited by examiner

*Primary Examiner* — John Fitzgerald
*Assistant Examiner* — Gregory J Redmann

(57) ABSTRACT

A process to monitor unwanted formation of a polymer having internal mechanical strain is disclosed. The acoustic emission generated by polymer formation is detected by one or more acoustic sensors attached to a piece of equipment.

10 Claims, No Drawings

PROCESS TO MONITOR UNWANTED FORMATION OF A POLYMER HAVING INTERNAL STRAIN BY ACOUSTIC EMISSION ANALYSIS

CROSS-REFERENCE TO RELATED APPLICATIONS

This application claims the benefit of PCT/EP2008/050141, filed Jan. 1, 2008, which claims priority from EP 07100265.3, filed Jan. 9, 2007.

FIELD OF THE INVENTION

The present invention is a process to monitor unwanted formation of a polymer having internal mechanical strain. By way of example of said polymers having internal mechanical strain are the popcorn polymers. Popcorn polymers are known to form from all manner of organic material, particularly olefinically unsaturated monomers, including olefins and diolefins; especially susceptible are the conjugated diolefins, e.g. butadiene and isoprene, and vinyl compounds, e.g. styrenes and acrylates. Known as popcorn polymers because they resemble popped corn, these polymers are also referred to in the art as sponge polymers, granular polymers, cauliflower-like polymers, nodular polymers, fluffy polymers, proliferous polymers, and crusty polymers. Popcorn polymer has been considered to occur from spontaneous monomer polymerization. It can occur in both liquid phase and vapor phase, and at any stage of use or handling of the monomer, e.g. recovery, separation, manufacturing, purification, storage, etc. High concentrations of monomer are particularly favorable for its formation.

BACKGROUND OF THE INVENTION

Many olefinically unsaturated organic monomers, for example styrene (with the impact of impurities such as, by way of example, divinylbenzene traces) and especially dienes having conjugated double bonds, such as 1,3-butadiene or isoprene, are prone to the spontaneous undesirable formation of popcorn polymers, for example during the storage and the transportation of these monomers, their recovery or further processing. These popcorn polymers are usually highly crosslinked, insoluble materials, which form foamy, crusty polymer granules having a cauliflower like structure on the walls of tanks, pipework, apparati and reactors.

Popcorn polymerization can result from the action of a variety of factors on the monomer concerned, for example oxygen, heat and rust as well as popcorn polymer particles already present in the monomer, which catalyze popcorn polymer formation. Specifically, it appears that the presence of one or more initiators e.g. water, oxygen, hydrogen peroxide results in the formation of popcorn polymer "seeds" in the organic material. The seeds themselves then perpetuate polymerization, without further requiring an initiator and/or a crosslinking agent; they serve as sites for further polymerization. As the particular mechanism, it is believed that monomer diffuses through the surface of the growing polymer mass, and is added to the polymer at the center thereof. For this reason, such polymerization is referred to as occurring "from the inside out." Consequently, there is continued incorporation of monomer into the polymer phase, leading to buildup of the popcorn polymer. This continuous incorporation of monomer, added with the crosslinking, implies high internal mechanical strains. These strains explain why the polymers breaks, producing new popcorn polymer seeds. The result is a hard polymeric foulant, which can cause serious equipment and safety concerns if left unchecked.

A particular problem attendant upon popcorn polymer formation is its extreme resistance to deactivation, once present in a system. Some of the seeds become attached to the processing and handling equipment, and cannot be readily removed by mechanical means; moreover, being insoluble in most common solvents, they are virtually impossible to wash out by use of such solvents. Even after equipment and storage facilities have been cleaned thoroughly, residual particles of popcorn polymer remain, and promote unwanted polymer growth. Trace particles remaining in the equipment will stay active for long periods without the presence of monomer, and serve to initiate polymerization when once again contacted therewith.

Popcorn polymer formation is especially critical in the case of conjugated diene monomers, such as 1,3-butadiene or isoprene. Here, popcorn polymerization may be responsible for pipework and reactors becoming plugged and for tank charges polymerizing wholesale and the tanks concerned bursting as a consequence.

U.S. Pat. No. 5,072,064 A relates to Inhibition of popcorn polymer growth by treatment with a compound including a Group IV element, and at least one hydrogen bonded to the Group IV element. This compound can be admixed with organic material from which popcorn polymer is formed, or added to a system for the recovery, use or storage of such organic material.

US 2001-005248 A1 relates to a process for the inhibition of popcorn polymer growth in unstabilized material which comprises olefinically unsaturated organic compounds and is prone to form popcorn polymer, which comprises adding to said material an effective amount of an aliphatic alcohol of the formula ROH where R is a straight-chain, branched or cyclic $C_3$-$C_{20}$-alkyl or alkylene group, the alkylene group bearing a second hydroxyl group.

Other patents such as U.S. Pat. No. 6,348,598, U.S. Pat. No. 6,495,065, US 2004-0019165, US 2004-0267078 and US 2005-0004413 have described similar stabilization.

Nevertheless even the addition of a stabilizer is not enough to prevent popcorn polymerization particularly in places where the monomer stays or circulates at low speed. By way of example such places are the manholes, the shell side of heat exchangers, dead legs such as pipe to safety valves and storage facilities. It is necessary to clean in due time said equipment and storage facilities to prevent plugging or destruction thereof.

U.S. Pat. No. 5,734,098 explains that during the recovery of light hydrocarbons in ethylene plants, butadiene plants, isoprene plants and the like, distillation towers and associated equipment like heat exchangers and reboilers are fouled by the thermal and/or oxidative polymerization of reactive olefins like butadiene. By placing thickness-shear mode resonator devices into the vapor space, beneath select trays in the tower, the probes could be used to detect the formation of foulant such as the popcorn polymer. Thickness-shear mode resonators may be placed in the vapor space of towers such as primary fractionators, depropanizers, debutanizers, and butadiene purification columns. The thickness-shear mode resonators would be sensitive to the formation of viscoelastic polymer in the vapor phase which would deposit on the resonators. This device is deemed to measure the thickness of the popcorn polymer. This process doesn't work efficiently mainly because the popcorn polymer has not a regular thickness like the fouling caused by cooling water.

It has been discovered that during the popcorn polymerization, as well as any polymer with internal mechanical strain, there is an acoustic emission which can be detected by an acoustic sensor such as a microphone. Advantage of said process is that the acoustic sensor has not to be in direct contact with the popcorn, it can be attached on the outside of the volume in which the unwanted formation of polymer occurs, e.g. the manhole, the exchanger's shell, the pipes, the distillation columns or a storage facility. Advantage of said early detection is that operators can remove said popcorn polymers before a complete plugging or a destruction of a piece of equipment.

The prior art has already described acoustic emissions to monitor processes in which the purpose is to make a polymerization, which means it is exactly the contrary of the present invention.

DD 241480 describes a vinyl acetate emulsion polymerization process. Said polymerization generates an acoustic emission recorded by means of transducers of the basic frequency 100 kHz to 1 MHz, thus said polymerization can be followed. In said emulsion polymerization the polymer is in the form of particles and the motion of particles in the liquid generates an acoustic emission. This is not the acoustic emission generated by the internal strain and breakage of a polymer.

F. Ferrer, E. Schille, D. Verardo and J. Goudiakas have described the sensitivity of acoustic emission for the detection of stress corrosion cracking during static U-bend tests on a 316 L stainless steel in hot concentrated magnesium chloride media, (Journal of Materials Science, Volume 37, Number 13/July, 2002 Pages 2707-2712, Springer Netherlands).

GB 2038851 describes a method of, and the apparatus for, continuously measuring the polymerisation process of vinyl chloride and other monomers, using acoustic principles. An acoustic transducer located in polymerising medium responds to acoustical energy emission from chemical and physical interactions in the polymerisation medium. The transduced signal is acoustically coupled via a scanning sound wave-guide and the resulting electrical signal is relayed via wires to a spectrum analyser which provides an indication of a particular polymerisation process. The waveguide and sensor are located in the polymerisation medium. A piezoelectric twin generates the signal. In said emulsion polymerization the polymer is in the form of particles and the motion of particles in the liquid generates an acoustic emission. The electric terminals of the piezoceramic twin are connected e.g. via a preamplifier to a selective microvoltmeter or to a synchronous detector of a decrementmeter. Due to the pulsating flow of the polymerization system in the reactor space the scanning sound wave-guide is made to oscillate in damped oscillations of mostly own frequency, the logarithmic decrement of which is in correlation with changes in the viscosity of the polymerizing product. Said damped oscillations have nothing to see with our acoustic sensor which doesn't oscillate in the polymerization medium.

WO 03 051929 provides a method of evaluating a commercial gas-phase fluid bed reactor continuity by measuring at least one system variable, filtering the data to demodulate a time series and calculating a signal, which is indicative of reactor continuity. System variables comprise an acoustic emission, a differential pressure, a bed total weight/volume, a fluidized bulk density, a static voltage and a reactor wall temperature. In said gas phase polymerization the polymer is in the form of particles or powder, it has nothing to see with the acoustic emission generated by the internal strain and breakage of a polymer.

BRIEF SUMMARY OF THE INVENTION

The present invention concerns a process to monitor unwanted formation of a polymer having internal mechanical strain wherein acoustic emission generated by said polymer formation is detected by one or more acoustic sensors attached to a piece of equipment.

Advantageously said acoustic sensor is located outside of the volume in which the unwanted formation of polymer occurs. By way of example the acoustic sensor can be located in a thermowell (glove thinger).

It would not depart of the scope of the invention to have the acoustic sensor(s) located in the volume in which the unwanted formation of polymer occurs but it could lead to technical problems.

In a particular embodiment said polymers having internal mechanical strain are cross-linked polymers.

In a more particular embodiment said polymers having internal mechanical strain are popcorn polymers.

The present invention also relates to a device to carry-out the above process.

DETAILED DESCRIPTION OF THE INVENTION

As regards the monomer which polymerize to make polymers having internal mechanical strain mention may be made of vinyl monomers in general, and not only to a single vinyl monomer but also to a mixture of two or more vinyl monomers. Such vinyl monomer may be $\alpha,\beta$-unsaturated carboxylic acids and esters thereof, ethylene, propylene, 1,3-butadiene, isoprene, dimethyl-2,3-buta-1,3-diene, chloroprene, bromoprene, styrene, divinylbenzene, styrene containing traces of divinylbenzene, vinyltoluene, vinyl chloride and the like. $\alpha,\beta$-unsaturated carboxylic acids and esters thereof include, for example, acrylic acid, methyl acrylate, ethyl acrylate, n-butyl acrylate, i-butyl acrylate, stearyl acrylate, 2-ethylhexyl acrylate, 2-hydroxyethyl acrylate, 2-hydroxypropyl acrylate, 4-hydroxybutyl acrylate, ethylene glycol diacrylate, glycidyl acrylate, 2-ethoxyethyl acrylate, tetrahydrofurfuryl acrylate, cyclohexyl acrylate, benzyl acrylate, allyl acrylate, t-butyl acrylate, 1,6-hexanediol diacrylate, dimethylaminoethyl acrylate, methacrylic acid, methyl methacrylate, ethyl methacrylate, n-butyl methacrylate, i-butyl methacrylate, stearyl methacrylate, 2-ethylhexyl methacrylate, 2-hydroxyethyl methacrylate, 2-hydroxypropyl methacrylate, ethylene glycol dimethacrylate, glycidyl methacrylate, 2-ethoxyethyl methacrylate, cyclohexyl methacrylate, benzyl methacrylate, allyl methacrylate, t-butyl methacrylate, dimethylaminoethyl methacrylate, phenyl methacrylate, crotonic acid, methyl crotonate, ethyl crotonate, itaconic acid, dimethyl itaconate, methyl $\alpha$-hydroxyethylacrylate, ethyl $\alpha$-hydroxyethylacrylate. Mention may be made also of ketones such as methyl vinyl ketone, and nitriles such as acrylonitrile. It is a matter of course that the present invention is not limited thereto.

In a particular embodiment the present invention relates to the above monomers leading to cross-linked polymers. In a more particular embodiment the present invention relates to the above monomers leading to popcorn polymers. By way of example said monomers leading to popcorn polymers are 1,3-butadiene, isoprene, dimethyl-2,3-buta-1,3-diene, chloroprene, bromoprene, styrene containing impurities, divinylbenzene and styrene containing traces of divinylbenzene.

The continuous incorporation of monomer in the polymer, added to the crosslinking, implies high internal mechanical strains. These strains explain why the polymers break, producing new polymer seeds, by way of example, popcorn polymer seeds. The sudden break of the polymer produces shots in the polymer and on the metallic structure of the equipment. The invention uses this specific property of polymer with internal mechanical strain in order to measure the activity of said polymer.

The acoustic sensor attached to a piece of equipment, by way of example a manhole, advantageously turns the acoustic emission to an electrical or digital signal. Most of time this acoustic emission is ultrasonic. Said signal is advantageously connected to means for filtering in order to discriminate against usual noise of said equipment. Advantageously the above signal is connected to means to display the frequency, the energy level (can be measured in Decibels (dB)) and amplitude. The acoustic sensor can be attached by any means to the piece of equipment, by way of example by a magnet. Advantageously there is an acoustic sensor attached at any piece of equipment where polymer with internal mechanical strain may occur. By way of examples microphones of trade mark Vallen systeme type AMSY4 made by the company Vallen-Systeme Gmbh at D-82057 Icking (Munich) in Germany have been used on manholes in a butadiene plant. In a specific embodiment the capture threshold ranges from 30 to 50 dB and is advantageously around 40 dB. In a specific embodiment all these acoustic sensors are connected to means for filtering in order to discriminate against usual noise of said equipment and connected to means to display for each acoustic sensor the frequency, the energy level and amplitude. These measurements are compared to previous typical recordings from said acoustic sensor attached to said piece of equipment: one recording when there is formation of a polymer having internal mechanical strain and another one when there is no formation of a polymer having internal mechanical strain. Advantageously said filtering, display of measurements and comparison with previous records are made by a computer. In a preferred embodiment said computer sets an alarm in the control room of the plant, thus operators know that polymers having internal mechanical strain are under formation and can decide to reduce capacity and/or to clean said piece of equipment in which said polymers are present.

In a specific and preferred embodiment the acoustic sensor is a resonant piezo-electric transducer comprising filtering means to select a frequency range. The formation of the polymer having internal mechanical strain produce shots, said shots are converted to a signal by the resonant piezo-electric transducer. Advantageously service temperature of said resonant piezo-electric transducer is up to 200° C.

Advantageously said resonant piezo-electric transducer is connected to a conditioner unit comprising means for filtering and an operational preamplifier. Said filtering means select the frequency range characterizing formation of a specific polymer. The man skilled in the art can find easily said frequency range by comparison of signal recordings made in various locations of a piece of equipment (e.g. a column or a heat exchanger) or in various pieces of equipment. Optionally he takes account of the usual noise of said piece of equipment. As regards butadiene the frequency is ranging from 10 to 100 kHz and more often around 40 kHz. The output signal from said filtering means is damped oscillations.

Advantageously said conditioner unit is connected to a unit (or comprises a unit) in which there is at least one adjustable threshold level and advantageously a plurality of cascaded threshold levels. The man skilled in the art can easily determine by experiment the shape of such damped oscillations for any kind of polymer and a piece of equipment. Then he sets and adjusts one or more threshold levels.

By way of example, 3 levels are fixed. Level 1 is the higher, level 2 is lower and then level 3 lower than level 2. The damped oscillations are such (by way of example) that there are two oscillations above level 1, one oscillation above level 2 (but under level 1) and 2 oscillations above level 3 (but under level 2). It is decided that this corresponds to one shot in the polymer formation.

Optionally a pulse counter is connected to the conditioner unit. Whenever an oscillation is over a threshold level a pulse is counted. The number of pulse for every threshold level is displayed and/or recorded. Optionally the time during which an oscillation is over a threshold level is counted. Optionally the time during which an oscillation is over a threshold level is compared with a time set. Analysis of these data gives a good prediction of the polymer formation.

Advantageously display of measurements and analysis of data are made by a computer. In a preferred embodiment said computer sets an alarm in the control room of the plant, thus operators know that polymers having internal mechanical strain are under formation and can decide to reduce capacity and/or to clean said piece of equipment in which said polymers are present.

It has been established for butadiene that after the filtering the captured signals have:
- a signal to noise ratio from 1.2 to 100, often from 1.5 to 10 and more often from 2 to 4.
- a frequency centroid ranging from 80 to 350 kHz,
- a duration before attenuation, linked to the acoustic properties of the equipment, of less than 5000 µs, advantageously less than 4000 µs, preferably less than 3500 µs and more preferably between 2000 and 3500 µs,
- a number of shots at each emission induced by the presence of popcorn polymer that breaks less than 400, advantageously less than 300, preferably less than 200 and more preferably between 50 and 200,
- a real acoustic energy ranging from 10 e.u. to $10^E5$ e.u. (1 e.u.=1 E–18 J).

About the number of shots when the polymer breaks it is not a one shot break but a rupture which propagates in chain along the polymer similar to the tensile strength along the rupture line in an earthquake.

The present invention also relates to a device to carry-out the above process said device comprising:
- one or more acoustic sensors attached to a piece of equipment turning the acoustic emission to an electrical or digital signal,
- means for filtering said signal in order to discriminate against usual noise of said equipment and connected to means to display the frequency, the energy level and amplitude,
- means to compare said measurements to previous typical recordings from said acoustic sensor attached to said piece of equipment: one recording when there is formation of a polymer having internal mechanical strain and another one when there is no formation of a polymer having internal mechanical strain.

By way of example in a butadiene plant acoustic sensors are attached to the various pieces of equipment in which popcorn polymers may occur. Said acoustic sensors are connected to the means for filtering, the means to display and the means to compare measurements to previous typical recordings and said means are located in a control room.

The present invention also relates in a preferred embodiment to a device to carry-out the above process said device comprising:
- a resonant piezo-electric transducer attached to a piece of equipment,
- optionally a conditioner unit, connected to the previous transducer, said conditioner unit comprising means for filtering and an operational preamplifier, optionally a unit, connected to said conditioner unit, in which there is at least one adjustable threshold level (unless the conditioner unit comprises said adjustable threshold level), optionally a pulse counter connected to the conditioner unit comprising at least one adjustable threshold level.

The invention claimed is:

1. A process to monitor unwanted formation of a polymer having internal mechanical strain, wherein acoustic emission generated by polymer formation is detected by one or more acoustic sensors attached to a piece of equipment wherein each acoustic sensor turns an acoustic emission into an electrical or digital signal, wherein each signal is connected to a filter to discriminate against usual noise emitted from the equipment and is connected to a display, wherein the display transmits measurements comprising frequency, energy level and amplitude, wherein the measurements are compared to previous recordings from the acoustic sensor, wherein the previous recordings comprise a first recording when there is formation of a polymer having internal mechanical strain and a second recording when there is no formation of a polymer having internal mechanical strain.

2. A process to monitor unwanted formation of a polymer having internal mechanical strain, wherein acoustic emission generated by polymer formation is detected by one or more acoustic sensors attached to a piece of equipment, the acoustic sensor is a resonant piezo-electric transducer comprising a filter adapted to select a frequency range and the transducer is connected to a conditioner adapted to filter and comprising an operational preamplifier.

3. The process of claim 2, wherein each acoustic sensor turns an acoustic emission into an electrical or digital signal.

4. The process of claim 2, wherein the filter is adapted to select a frequency range characterizing formation of a specific polymer.

5. The process of claim 2, wherein an output signal from the filter comprises damped oscillations.

6. The process of claim 2, wherein the conditioner is connected to a unit comprising at least one adjustable threshold level.

7. The process of claim 2 further comprising a pulse counter connected to the condition, wherein the pulse counter is adapted to count a pulse whenever an oscillation exceeds a threshold level.

8. The process of claim 2, wherein the polymer comprises cross-linked polymers.

9. The process of claim 2, wherein the polymer comprises popcorn polymers.

10. The process of claim 9, wherein the polymers are derived from 1,3-butadiene, isoprene, dimethyl-2,3-buta-1,3-diene, chloroprene, bromoprene, styrene containing impurities, divinylbenzene or styrene containing traces of divinylbenzene.

* * * * *